Figure 1:
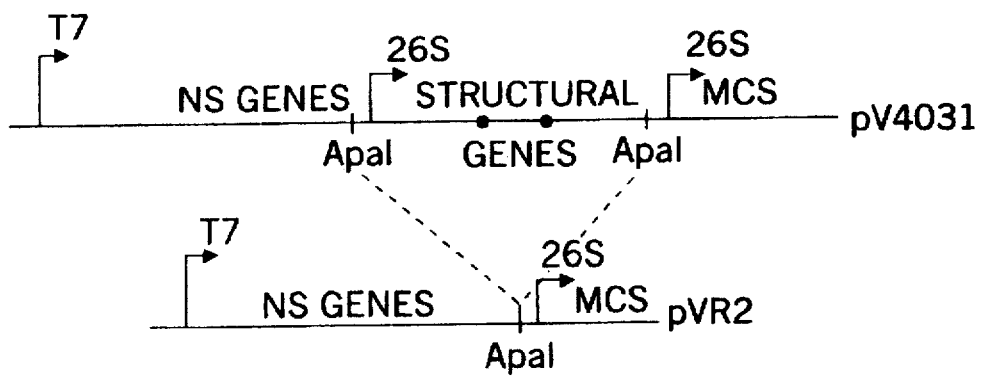

US005792462A

United States Patent [19]
Johnston et al.

[11] Patent Number: 5,792,462
[45] Date of Patent: Aug. 11, 1998

[54] ALPHAVIRUS RNA REPLICON SYSTEMS

[75] Inventors: Robert E. Johnston; Nancy L. Davis, both of Chapel Hill, N.C.; Jonathan F. Smith, Sabillasville, Md.; Peter Pushko, Frederick, Md.; Michael Parker, Frederick, Md.; George Ludwig, Frederick, Md.

[73] Assignees: University of North Carolina at Chapel Hill, Chapel Hill, N.C.; The United States of America as represented by the Secretary of the Army, Washington, D.C.

[21] Appl. No.: 448,630

[22] Filed: May 23, 1995

[51] Int. Cl.$^6$ .................. A61K 39/295; C12N 5/10; C12N 7/01; C12N 15/00

[52] U.S. Cl. .................. 424/199.1; 435/325; 435/235.1; 435/172.3; 435/320.1; 424/93.2

[58] Field of Search .................. 424/218.1, 93.2, 424/93.3, 93.6, 199.1; 435/69.1, 172.1, 252.3, 335.1, 236, 69.3, 172.3, 320.1, 325; 536/23.76

[56] References Cited

U.S. PATENT DOCUMENTS

| | | |
|---|---|---|
| 4,650,764 | 3/1987 | Temin et al. |
| 5,185,440 | 2/1993 | Davis et al. |
| 5,217,879 | 6/1993 | Huang et al. |

FOREIGN PATENT DOCUMENTS

| | | | |
|---|---|---|---|
| WO 92/10578 | 6/1992 | WIPO. | |
| WO 95/07994 | 3/1995 | WIPO | C12N 15/85 |

OTHER PUBLICATIONS

Morgenstein et al. Advanced Mammalian Gene Transfer: High Titer Retroviral Vectors with Multiple Drug Selection Markers and a Complementary Helper–Free Packaging Cell Line. Nuclear and Research 18:3587–3596, 1990.

Suomalainen et al. Spike Protein–Nucleocepsid Interactions Drive the Budding of Alphaviruses. J: Virol 66:4737–4747, 1992.

Davis et al Virology 212:102–110 1995.

N.L. Davis et al: Attenuating Mutations in the E2 Glycoprotein Gene of Venezuelan Equine Encephalitis Virus: Construction of Single and Multiple Mutants in a Full-Lenght cDNA Clone; *Virology* 183 20–31 (1991).

Davis et al: A Genetically Engineered Live Virus Vaccine for Venezuelan Equine Encephalitis; *J. Cell Biochemistry* Supplement O No. 17 Part D, issued 1993, Abstract N404.

R.J. Schoepp and R.E. Johnston; Directed Mutagenesis of a Sindbis Virus Pathogenesis Site; *Virology* 193, pp. 149–159 91993).

J.M. Polo and R.E. Johnston; Attenuating Mutations in Glycoproteins E1 and E2 of Sindbis Virus Produce a Highly Attenuated Strain When Combined in Vitro; *Journal of Virology* 64 No. 9; pp. 4438–4444 (1990).

P.J. Bredenbeek et al; Sindbis Virus Expression Vectors: Packaging of RNA Replicons by Using Defective Helper RNAs; *Journal of Virology* 67 No. 11; pp. 6439–6446 (1993).

Liljestrom et al.; A New Generation Of Animal Cell Expression Vectors Based On The Semliki Forest Virus Replicon; *Bio/Technology,* vol. 9, Dec. 1991, pp. 1356–1361.

Strauss et al.; The Alphaviruses: Gene Expression, Replication, and Evolution; *Microbiological Reviews,* Sep. 1994; pp. 491–562.

Russell, et al., *Sindbis Virus Mutations Which Coordinately Affect Glycoprotein Processing, Penetration, And Virulence In Mice,* Journal of Virology, vol. 63, No. 4, Apr. 1989, pp. 1619–1629.

*Primary Examiner*—Mary E. Mosher
*Attorney, Agent, or Firm*—Myers Bigel Sibley & Sajovec, P.A.

[57] ABSTRACT

The present invention provides a helper cell for expressing an infectious, replication defective, alphavirus particle in an alphavirus-permissive cell. The helper cell includes (a) a first helper RNA encoding (i) at least one alphavirus structural protein, and (ii) not encoding at least one alphavirus structural protein; and (b) a second helper RNA separate from the first helper RNA, the second helper RNA (i) not encoding the alphavirus structural protein encoded by the first helper RNA, and (ii) encoding the at least one alphavirus one structural protein not encoded by the first helper RNA, such that all of the alphavirus structural proteins assemble together into alphavirus particles in the cell. Preferably, the helper cell also includes a replicon RNA encoding an alphavirus packaging sequence and an inserted heterogeneous RNA.

27 Claims, 2 Drawing Sheets

FIG. 3A

MOUSE 1; INOCULATION WITH 4x10e+5 IU

- ○— ANTIBODY TO LASSA N
- ■— ANTIBODY TO VEE

BOOSTER INJECTION

ELISA TITER vs DAYS POST INOCULATION

FIG. 3B

MOUSE 2; INOCULATION WITH 4x10e+7 IU

- ○— ANTIBODY TITER TO LASSA N
- ■— ANTIBODY TITER TO VEE

BOOSTER INJECTION

ELISA TITER vs DAYS POST INOCULATION

ALPHAVIRUS RNA REPLICON SYSTEMS

This invention was made with Government support under Grant numbers DAMD17-91-C-1092 and 9113-ARG-0610 from the Department of the Army. The Government has certain rights to this invention.

FIELD OF THE INVENTION

The present invention relates to recombinant DNA technology, and in particular to introducing and expressing foreign DNA in a eukaryotic cell.

BACKGROUND OF THE INVENTION

The Alphavirus genus includes a variety of viruses all of which are members of the Togaviridae family. The alphaviruses include Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebarn virus, Mayaro virus, Una virus, Aura virus, Whataroa virus, Babanki virus, Kyzyla-gach virus, Highlands J virus, Fort Morgan virus, Ndumu virus, and Buggy Creek virus. The viral genome is a single-stranded, messenger-sense RNA, modified at the 5'-end with a methylated cap, and at the 3'-end with a variable-length poly (A) tract. Structural subunits containing a single viral protein, C, associate with the RNA genome in an icosahedral nucleocapsid. In the virion, the capsid is surrounded by a lipid envelope covered with a regular array of transmembranal protein spikes, each of which consists of a heterodimeric complex of two glycoproteins, E1 and E2. See Pedersen et al., *J. Virol.* 14:40 (1974). The Sindbis and Semliki Forest viruses are considered the prototypical alphaviruses, and have been studied extensively. See Schlesinger The Togaviridae and Flaviviridae, Plenum Publishing Corp., New York (1986). The VEE virus has been studied by the present inventors. See U.S. Pat. No. 5,185,440 to Davis et al.

The study of these virus has led to the development of beneficial techniques for vaccinating against the alphavirus diseases, and other diseases through the use of alphavirus vectors for the introduction of foreign DNA. See U.S. Pat. No. 5,185,440 to Davis et al., and PCT Publication WO 92/10578. The introduction of foreign DNA into eukaryotic cells has become a topic of increasing interest. It is well known that live, attenuated viral vaccines are among the most successful means of controlling viral disease. However, for some virus pathogens, immunization with a live virus strain may be either impractical or unsafe. One alternative strategy is the insertion of sequences encoding immunizing antigens or such agents into a vaccine strain of another virus. One such system utilizing a live VEE vector is described in U.S. Pat. No. 5,505,947 to Johnston, et al. Another such system is described by Hanhn et al., *Proc. Natl. Acad. Sci. USA* 89:2679 (1992), wherein Sindbis virus constructs which express a truncated form of the influenza hemagglutinin protein. Unfortunately, relatively few such systems are currently available.

Accordingly there remains a need in the art for nucleic acid sequences encoding foreign antigens into a vaccine strain of a virus which may be utilized as a vaccine for the foreign antigen, and/or the viral vector itself.

SUMMARY OF THE INVENTION

As a first aspect, the present invention provides a helper cell for expressing an infectious, replication defective, alphavirus particle in an alphavirus-permissive cell. The helper cell includes (a) a first helper RNA encoding (i) at least one alphavirus structural protein, and (ii) not encoding at least one alphavirus structural protein; and (b) a second helper RNA separate from the first helper RNA, the second helper RNA (i) not encoding the at least one alphavirus structural protein encoded by the first helper RNA, and (ii) encoding at least one alphavirus structural protein not encoded by the first helper RNA, such that all of the alphavirus structural proteins assemble together into alphavirus particles in the cell. Preferably, the alphavirus packaging segment is deleted from at least the first helper RNA.

In a preferred embodiment, the helper cell also includes a replicon RNA, which encodes the alphavirus packaging segment and an inserted heterologous RNA. In the embodiment wherein the helper cell also includes a replicon RNA, the alphavirus packaging segment may be, and preferably is, deleted from both the first helper RNA and the second helper RNA. For example, in the embodiment wherein the helper cell includes a replicon RNA encoding the alphavirus packaging segment and an inserted heterologous RNA, the first helper RNA includes the alphavirus E1 glycoprotein and the alphavirus E2 glycoprotein, and the second helper RNA includes the alphavirus capsid protein. The replicon RNA, first helper RNA, and second helper RNA are all on separate molecules and are cotransfected into the host cell.

In an alternative embodiment, the helper cell includes a replicon RNA encoding the alphavirus packaging segment, an inserted heterologous RNA, and the alphavirus capsid protein encoded by the second helper RNA, and the first helper RNA includes the alphavirus E1 glycoprotein and the alphavirus E2 glycoprotein. Thus, the replicon RNA and the first helper RNA are on separate molecules, and the replicon RNA and the second helper RNA are on a single molecule. The heterologous RNA comprises a foreign RNA which encodes for proteins or peptides which are desireously expressed in the helper cell.

The RNA encoding the structural proteins, i.e., the first helper RNA and the second helper RNA, may advantageously include one or more attenuating mutations. In the preferred embodiment, at least one of the first helper RNA and the second helper RNA includes at least one attenuating mutation. The attenuating mutations provide the advantage that in the event of RNA recombination within the cell, the coming together of the structural and non-structural genes will produce a virus of decreased virulence.

As a second aspect, the present invention provides a method of making infectious, replication defective, alphavirus particles. The method includes transfecting a helper cell as given above with a replication defective replicon RNA, producing the alphavirus particles in the transfected cell, and then collecting the alphavirus particles from the cell. The replicon RNA encodes the alphavirus packaging segment and a heterologous RNA. The transfected cell further includes the first helper RNA and second helper RNA as described above.

As a third aspect, the present invention provides a set of RNAs for expressing an infectious, replication defective alphavirus. The set of RNAs comprises, in combination, (a) a replicon RNA encoding a promoter sequence, an inserted heterologous RNA, wherein RNA encoding at least one structural protein of the alphavirus is deleted from the replicon RNA so that the replicon RNA is replication defective, and (b) a first helper RNA separate from the replicon RNA, wherein the first helper RNA encodes in trans, the structural protein which is deleted from the replicon RNA and a promoter sequence. In this embodiment, it is preferred that an RNA segment encoding at least one of the structural proteins is located on an RNA other than the first helper RNA. Thus, for example, the set of RNAs may include a replicon RNA including RNA which encodes the alphavirus packaging sequence, the inserted heterologous RNA, and the alphavirus capsid protein, but both the alphavirus E1 glycoprotein and alphavirus E2 glycoprotein are deleted therefrom; and a first helper RNA includes RNA encoding both the alphavirus E1 glycoprotein and the alphavirus E2 glycoprotein.

In another embodiment, the set of RNAs also includes a second helper RNA separate from the replicon RNA and the first helper RNA. In this embodiment, the second helper RNA encodes, in trans, at least one structural protein, which is different from the structural protein encoded by the replicon RNA and by the first helper RNA. Thus, for example, the set of RNAs may include a replicon RNA including RNA which encodes the alphavirus packaging sequence, and the inserted heterologous RNA; a first helper RNA including RNA which encodes a promoter sequence and an RNA encoding both the alphavirus E1 glycoprotein and the alphavirus E2 glycoprotein; and a second helper RNA including RNA which encodes the alphavirus capsid protein, with the replicon RNA, the first helper RNA, and the second helper RNA being in trans from each other, on separate molecules.

As a fourth aspect, the present invention provides infectious VEE virus particles containing RNA encoding a promoter sequence, and an inserted heterologous RNA, and wherein RNA encoding at least one alphavirus structural protein is deleted from the RNA so that the RNA is replication defective.

As a fifth aspect, the present invention provides a pharmaceutical formulation comprising infectious alphavirus particles as described above, in an effective immunogenic amount in a pharmaceutically acceptable carrier.

The foregoing and other aspects of the present invention are explained in detail in the detailed description set forth below.

BRIEF DESCRIPTION OF THE DRAWINGS

FIG. 1 is a graphical representation of the pV4031 clone and the production of the pVR2 replicon.

FIG. 2 illustrates the construction of the double helper RNA system plasmids in accordance with the present invention. In the drawings designated P21-1 and P24-3, the dashed lines indicate structural proteins or portions thereof which are deleted in the plasmid. FIG. 2 also illustrates a single helper RNA system plasmid, and the construction of recombinant VEE clones containing heterologous genes. In this figure, "nsp" means non-structural protein.

FIG. 3 is a graphical representation of the results obtained in inoculating mice with the VEE replicon/Lassa N infectious particles produced by a single-helper RNA system, at two different dosage units. The top graph (FIG. 3A) represents results obtained with a low-dose inoculation with infectious particles. The bottom graph (FIG. 3B) illustrates results obtained with a high-dose inoculation with infectious particles.

DETAILED DESCRIPTION OF THE INVENTION

The term "alphavirus" has its conventional meaning in the art, and includes the various species of alphaviruses such as Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, South African Arbovirus No. 86, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, and Buggy Creek virus. The preferred alphavirus RNA transcripts for use in the present invention include VEE, Sindbis virus, South African Arbovirus No. 86 and Semliki Forest virus.

Alphavirus-permissive cells employed in the methods of the present invention are cells which, upon transfection with the viral RNA transcript, are capable of producing viral particles. Alphaviruses have a broad host range. Examples of suitable host cells include, but are not limited to Vero cells, baby hamster kidney (BHK) cells, and chicken embryo fibroblast cells.

The phrases "structural protein" or "alphavirus structural protein" as used herein refer to the encoded proteins which are required for replication of the RNA replicon, and include the capsid protein, E1 glycoprotein, and E2 glycoprotein. As described hereinabove, the structural proteins of the alphavirus are distributed among one or more helper RNAs (i.e., a first helper RNA and a second helper RNA). In addition, one or more structural proteins may be located on the same RNA molecule as the replicon RNA, provided that at least one structural protein is deleted from the replicon RNA such that the replicon and resulting alphavirus particle are replication defective. As used herein, the terms "deleted" or "deletion" mean either total deletion of the specified segment or the deletion of a sufficient portion of the specified segment to render the segment inoperative or nonfunctional, in accordance with standarg useage. See, e.g., U.S. Pat. No. 4,650,764 to Temin et al. The term "replication defective" as used herein, means that the replicon RNA cannot replicate in the host cell in the absence of the helper RNA. The replicon RNA is replication defection inasmuch as the replicon RNA does not include all of the alphavirus structural proteins required for replication, at least one of the required structural proteins being deleted therefrom.

The helper cell for expressing the infectious, replication defective alphavirus particle comprises a set of RNAs, as described above. The set of RNAs principly include a first helper RNA and a second helper RNA. The first helper RNA includes RNA encoding at least one alphavirus structural protein but does not encode all alphavirus structural proteins. In other words, the first helper RNA does not encode at least one alphavirus structural protein; the at least one non-coded alphavirus structural protein being deleted from the first helper RNA. In one embodiment, the first helper RNA includes RNA encoding the alphavirus E1 glycoprotein, with the alphavirus capsid protein and the alphavirus E2 glycoprotein being deleted from the first helper RNA. In another embodiment, the first helper RNA includes RNA encoding the alphavirus E2 glycoprotein, with the alphavirus capsid protein and the alphavirus E1 glycoprotein being deleted from the first helper RNA. In a third, preferred embodiment, the first helper RNA includes RNA encoding the alphavirus E1 glycoprotein and the alphavirus E2 glycoprotein, with the alphavirus capsid protein being deleted from the first helper RNA.

The second helper RNA includes RNA encoding at least one alphavirus structural protein which is different from the at least one structural protein encoded by the first helper RNA. Thus, the second helper RNA encodes at least one alphavirus structural protein which is not encoded by the at least one structural protein encoded by the first helper RNA. The second helper RNA does not encode the at least one alphavirus structural protein which is encoded by the first helper RNA, thus the first and second helper RNAs do not encode duplicate structural proteins. The second helper RNA encodes a different structural protein than that encoded by the first helper RNA. In the embodiment wherein the first helper RNA includes RNA encoding only the alphavirus E1 glycoprotein, the second helper RNA may include RNA encoding one or both of the alphavirus capsid protein and the alphavirus E2 glycoprotein which are deleted from the first helper RNA. In the embodiment wherein, the first helper RNA includes RNA encoding only the alphavirus E2 glycoprotein, the second helper RNA may include RNA encoding one or both of the alphavirus capsid protein and the alphavirus E1 glycoprotein which are deleted from the first helper RNA. In the embodiment wherein the first helper RNA includes RNA encoding both the alphavirus E1 glycoprotein and the alphavirus E2 glycoprotein, the second helper RNA may include RNA encoding the alphavirus capsid protein which is deleted from the first helper RNA.

In one embodiment, the packaging segment or "encapsidation sequence" is deleted from at least the first helper RNA. In a preferred embodiment, the packaging segment is deleted from both the first helper RNA and the second helper RNA.

In the preferred embodiment wherein the packaging segment is deleted from both the first helper RNA and the second helper RNA, preferably the helper cell contains a replicon RNA in addition to the first helper RNA and the second helper RNA. The replicon RNA encodes the packaging segment and an inserted heterologous RNA. The inserted heterologous RNA may be RNA encoding a protein or a peptide. Typically, the inserted heterologous RNA encodes a protein or a peptide which is desirously expressed by the host, alphavirus-permissive cell, and includes the promoter and regulatory segments necessary for the expression of that protein or peptide in that cell. Examples of suitable inserted heterologous RNA include viral RNA from a wide variety of viruses including, but not limited to Lassa fever virus, Lentivirus, Equine infectious anemia, Influenza virus, Corona virus, and HIV. Examples of suitable viral RNA genes that may be used to provide the inserted heterologous RNA include, but are not limited to the Lassa fever virus nucleocapsid protein gene, the Lassa fever envelope glycoprotein gene, the influenza hemagglutinin gene, the influenza nucleoprotein gene, the Lentivirus glycoprotein envelope gene, the human corona virus envelop glycoprotein gene, the HIV envelope GP160 gene, and the HIV matrix capsid fusion gene. The replicon RNA may also encode the alphavirus nonstructural proteins, although it is not required.

In a preferred embodiment, the replicon RNA, the first helper RNA and the second helper RNA are provided on separate molecules such that a first molecule, i.e., the replicon RNA, includes RNA encoding the packaging segment and the inserted heterologous RNA, a second molecule, i.e., the first helper RNA, includes RNA encoding at least one but not all of the required alphavirus structural proteins, and a third molecule, i.e., the second helper RNA, includes RNA encoding at least one but not all of the required alphavirus structural proteins. For example, in one preferred embodiment of the present invention, the helper cell includes a set of RNAs which include (a) a replicon RNA including RNA encoding an alphavirus packaging sequence and an inserted heterologous RNA, (b) a first helper RNA including RNA encoding the alphavirus E1 glycoprotein and the alphavirus E2 glycoprotein, and (c) a second helper RNA including RNA encoding the alphavirus capsid protein so that the alphavirus E1 glycoprotein, the alphavirus E2 glycoprotein and the capsid protein assemble together into alphavirus particles in the host cell.

In an alternate embodiment, the replicon RNA and the first helper RNA are on separate molecules, and the replicon RNA and the second helper RNA are on a single molecule together, such that a first molecule, i.e., the first helper RNA, including RNA encoding at least one but not all of the required alphavirus structural proteins, and a second molecule, i.e., the replicon RNA and second helper RNA, including RNA encoding the packaging segment, the inserted heterologous DNA and the capsid protein. Thus, the capsid protein is encoded by the second helper RNA, but the second helper RNA is located on the second molecule together with the replicon RNA. For example, in one preferred embodiment of the present invention, the helper cell includes a set of RNAs including (a) a replicon RNA including RNA encoding an alphavirus packaging sequence, an inserted heterologous RNA, and an alphavirus capsid protein, and (b) a first helper RNA including RNA encoding the alphavirus E1 glycoprotein and the alphavirus E2 glycoprotein so that the alphavirus E1 glycoprotein, the alphavirus E2 glycoprotein and the capsid protein assemble together into alphavirus particles in the host cell.

In one preferred embodiment of the present invention, the RNA encoding the alphavirus structural proteins, i.e., the capsid, E1 glycoprotein and E2 glycoprotein, contains at least one attenuating mutation. The phrases "attenuating mutation" and "attenuating amino acid," as used herein, mean a nucleotide mutation or an amino acid coded for in view of such a mutation which result in a decreased probability of causing disease in its host (i.e., a loss of virulence), in accordance with standard terminology in the art. See, e.g., B. Davis, et al., *Microbiology* 132 (3d ed. 1980), whether the mutation be a substitution mutation or an in-frame deletion mutation. The phrase "attenuating mutation" excludes mutations which would be lethal to the virus. Thus, according to this embodiment, at least one of the first helper RNA and the second helper RNA includes at least one attenuating mutation. In a more preferred embodiment, at least one of the first helper RNA and the second helper RNA includes at least two, or multiple, attenuating mutations. The multiple attenuating mutations may be positioned in either the first helper RNA or in the second helper RNA, or they may be distributed randomly with one or more attenuating mutations being positioned in the first helper RNA and one or more attenuating mutations positioned in the second helper RNA. Appropriate attenuating mutations will be dependent upon the alphavirus used. For example, when the alphavirus is VEE, suitable attenuating mutations may be selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine, or histidine as E2 amino acid 209; codons at E1 amino acid 272 which specify an attenuating mutation, preferably threonine or serine as E1 amino acid 272; codons at E1 amino acid 81 which specify an attenuating mutation, preferably isoleucine or leucine as E1 amino acid 81; and codons at E1 amino acid 253 which specify an attenuating mutation, preferably serine or threoinine as E1 amino acid 253.

In an alternate embodiment, wherein the alphavirus is the South African Arbovirus No. 86 (S.A.AR86), suitable attenuating mutations may be selected from the group consisting of codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid 304; codons at E2 amino acid position 314 which specify an attenuating amino acid, preferably lysine as E2 amino acid 314; codons at E2 amino acid position 376 which specify an attenuating amino acid, preferably alanine as E2 amino acid 376; codons at E2 amino acid position 372 which specify an attenuating amino acid, preferably leucine as E2 amino acid 372; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372. Suitable attenuating mutations useful in embodiments wherein other alphaviruses are employed are known to those skilled in the art. Attenuating mutations may be introduced into the RNA by performing site-directed mutagenesis on the cDNA which encodes the RNA, in accordance with known procedures. See, Kunkel, *Proc. Natl. Acad. Sci. USA* 82:488 (1985), the disclosure of which is incorporated herein by reference in its entirety. Alternatively, mutations may be introduced into the RNA by replacement of homologous restriction fragments in the cDNA which encodes for the RNA, in accordance with known procedures.

Preferably, the first helper RNA and the second helper RNA also include a promoter. It is also preferred that the replicon RNA also includes a promoter. Suitable promoters for inclusion in the first helper RNA, second helper RNA and replicon RNA are well known in the art. One preferred promoter is the 26S promoter for use when the alphavirus is VEE. In the system wherein the first helper RNA, the second helper RNA, and the replicon RNA are all on separate molecules, the promoters, if the same promoter is used for all three RNAs, provides a homologous sequence between the three molecules. It is also advantageous to employ different promoters on the first and second helper RNAs to provide further impediment to RNA recombination that might produce virulent virus.

The infectious, replication defective, alphavirus particles may be prepared according to the methods disclosed herein in combination with techniques known to those skilled in the art. The method includes transfecting an alphavirus-permissive cell with a replication defective replicon RNA including the alphavirus packaging segment and an inserted heterologous RNA, a first helper RNA including RNA encoding at least one alphavirus structural protein, and a second helper RNA including RNA encoding at least one alphavirus structural protein which is different from that encoded by the first helper RNA; producing the alphavirus particles in the transfected cell; and collecting the alphavirus particles from the cell. The step of transfecting the alphavirus-permissive cell can be carried out according to any suitable means known to those skilled in the art. For example, uptake of the RNA into the cells can be achieved by any suitable means, such as for example, by treating the cells with DEAE-dextran, treating the cells with "LIPOFECTIN®", and by electroporation, with electroporation being the currently preferred means of achieving RNA uptake into the alphavirus-permissive cells. These techniques are well known in the art. See e.g., U.S. Pat. No. 5,185,440 to Davis et al., and PCT Publication No. WO 92/10578 to Bioption AB, the disclosures of which are incorporated herein by reference in their entirety.

The step of producing the infectious viral particles in the cells may also be carried out using conventional techniques. See e.g., U.S. Pat. No. 5,185,440 to Davis et al., PCT Publication No. WO 92/10578 to Bioption AB, and U.S. Pat. No. 4,650,764 to Temin et al. (although Temin et al., relates to retroviruses rather than alphaviruses). The infectious viral particles may be produced by standard cell culture growth techniques.

The step of collecting the infectious alphavirus particles may also be carried out using conventional techniques. For example, the infectious particles may be collected by cell lysis, or collection of the supernatant of the cell culture, as is known in the art. See e.g., U.S. Pat. No. 5,185,440 to Davis et al., PCT Publication No. WO 92/10578 to Bioption AB, and U.S. Pat. No. 4,650,764 to Temin et al. (although Temin et al. relates to retroviruses rather than alphaviruses). Other suitable techniques will be known to those skilled in the art. Optionally, the collected infectious alphavirus particles may be purified if desired. Suitable purification techniques are well known to those skilled in the art.

Pharmaceutical formulations, such as vaccines, of the present invention comprise an immunogenic amount of the infectious, replication defective alphavirus particles as disclosed herein in combination with a pharmaceutically acceptable carrier. An "immunogenic amount" is an amount of the infectious alphavirus particles which is sufficient to evoke an immune response in the subject to which the pharmaceutical formulation is administered. An amount of from about $10^1$ to about $10^5$ plaque forming units per dose is believed suitable, depending upon the age and species of the subject being treated. Exemplary pharmaceutically acceptable carriers include, but are not limited to, sterile pyrogen-free water and sterile pyrogen-free physiological saline solution. Subjects which may be administered immunogenic amounts of the infectious, replication defective alphavirus particles of the present invention include but are not limited to human and animal (e.g., horse, donkey, mouse, hamster, monkeys) subjects. Administration may be by any suitable means, such as intraperitoneal or intramuscular injection.

The following examples are provided to illustrate the present invention, and should not be construed as limiting thereof. In these examples, nm means nanometer, mL means milliliter, pfu/mL means plaque forming units/milliliter, VEE means Venezuelan Equine Encephalitis virus, EMC means Encephalomyocarditis virus, BHK means baby hamster kidney cells, HA means hemagglutinin gene, GFP means green fluorescent protein gene, N means nucleocapsid, FACS means fluorescence activated cell sorter, and IRES means internal ribosome entry site. The expression "E2 amino acid (e.g., lys, thr, etc.) number" indicates the designated amino acid at the designated residue of the E2 gene, and is also used to refer to amino acids at specific residues in the E1 gene.

EXAMPLE 1

Construction of VEE Replicon

The VEE structural protein genes (C-PE2-6K-E1) were removed from a cDNA clone (pV4031) which contained two attenuating mutations (E2 lys 209, E1 thr 272), and a duplication of the 26S subgenomic RNA promoter sequence immediately downstream from the 3'-end of the E1 glycoprotein gene followed by a multiple cloning site as described in U.S. Pat. No. 5,505,947 to Johnston et al. pV4031 plasmid DNA is digested to completion with ApaI restriction enzyme, which cuts the VEE genomic sequence at nucleotide 7505 (numbered from the 5'-end of the genome sequence). A second recognition site for this enzyme is found in the duplicate 26S subgenomic promoter. Therefore, digestion of pV4031 with ApaI produces two DNA fragments, one containing the VEE nonstructural genes and a single copy of the 26S subgenomic RNA promoter followed by a multiple cloning site, and a second smaller fragment containing a 26S subgenomic RNA promoter followed by the VEE structural genes. The large fragment is isolated and religated to produce the replicon, pVR2. FIG. 1 is a graphical representation of the pV4031 clone and pVR2 replicon.

EXAMPLE 2

Construction of Helper Plasmids

The starting materials for the helper plasmids are four full-length cDNA clones: V3000, the virulent Trinidad donkey strain of VEE, the three clones with attenuating mutations, pV3014 (E2 lys 209, E1 thr 272), V3519 (E2 lys 76, E2 lys 209, E1 thr 272) and V3526 (deletion of E3 56–59, E1 ser 253), in the genetic background of Trinidad donkey strain VEE. Several different helper plasmids have been made by using unique or rare restriction sites in the full-length cDNA clone to delete portions of the nonstructural protein region. The full-length clone is digested with one or two restriction enzymes, the larger DNA fragment is isolated and then religated to form a functional plasmid. In vitro RNA transcripts from these plasmids upon transfection of tissue culture cells would not encode a functional RNA replication complex, and probably also would not include an encapsidation signal. The helper constructs differ in the size of the nonstructural gene deletion. The helper constructs are designated by the attenuated mutant clone used in their construction, and by the percentage of the nonstructural region deleted. The following helper constructs were generated:

| | | |
|---|---|---|
| V3014Δ520-7507(93%) | B3519Δ520-7507(93%) | V3526Δ520-7505(93%) |
| V3014Δ520-6965(87%) | B3519Δ1687-7507(78%) | |
| V3014Δ2311-7505(70%) | B3519Δ3958-7507(47%) | V3526Δ520-7505(93%) |
| V3014Δ3958-7505(47%) | B3519Δ1955-3359(19%) | |
| V3014Δ520-3954(46%) | | |
| V3014Δ1955-3359(19%) | | |
| V3014Δ1951-3359(19%) | | |
| V3014Δ2311-3055(10%) | | |
| V3014Δ2307-3055(10%) | | |

EXAMPLE 3

Construction of Bipartite RNA Helper Plasmids

Figure 2:
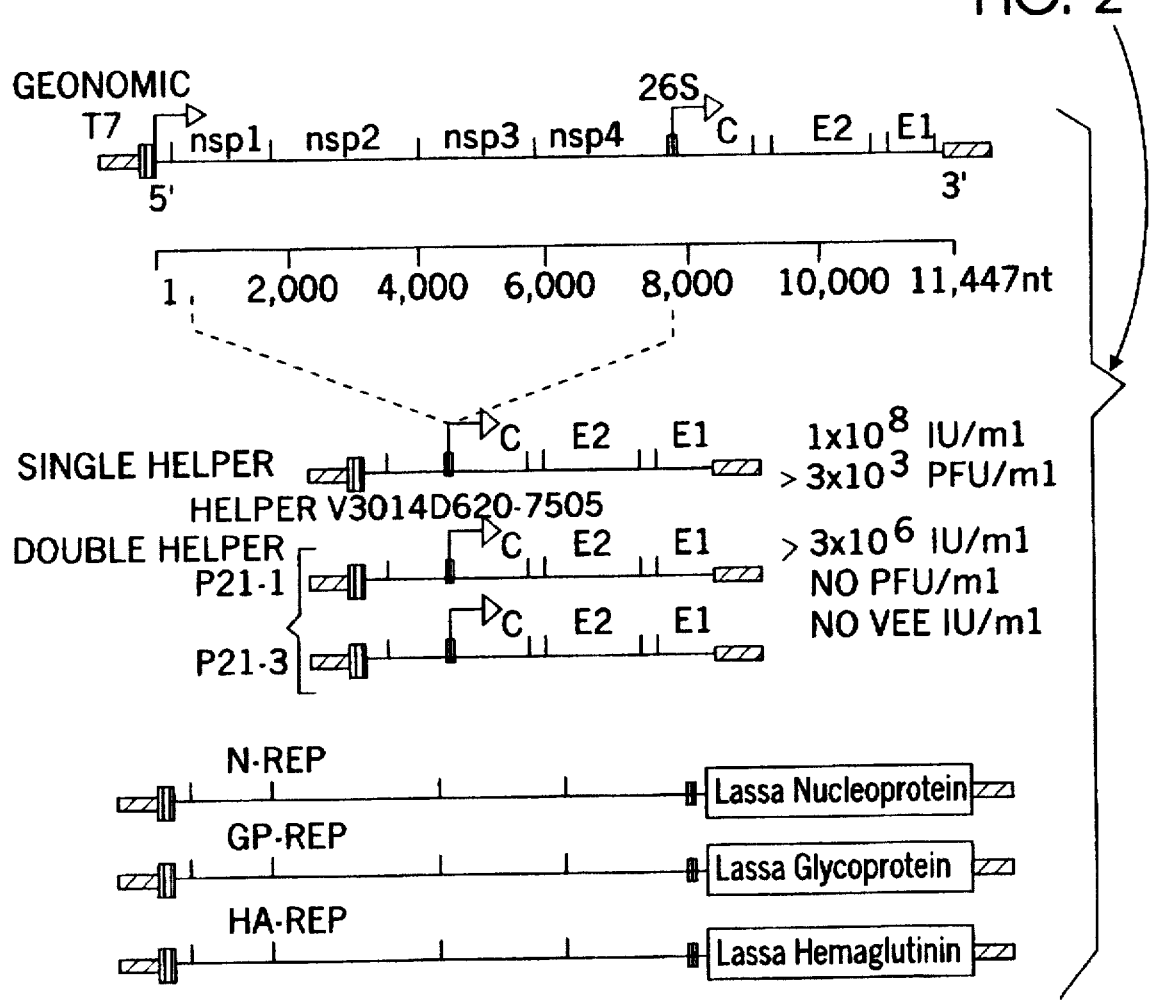

A bipartite helper system also is constructed as shown in FIG. 2. The V3014Δ520-7505(93%) helper is used to construct an additional deletion of the E2 and E1 glycoprotein genes by digestion with HpaI restriction enzyme and ligation, resulting in deletion of the sequence between nucleotide 8494 (in the E3 gene) and nucleotide 11,299 (near the 3'-end of the E1 gene). In vitro RNA transcripts of this plasmid when electroporated into BHK cells with a replicon RNA are replicated and transcribed to give a mRNA encoding only the C protein of VEE.

The second member of the bipartite helper is constructed from the same original helper plasmid by cleavage with Tth111I restriction enzyme (at nucleotide 7544) and SpeI restriction enzyme (at nucleotide 8389) and insertion of a synthetic double-stranded oligonucleotide with Tth111I and SpeI termini. The inserted sequence restored the downstream portion of the 26S promoter and an ATG initiation codon followed by a Ser codon, such that the first amino acid residue of E3 (Ser) is the first codon following the inserted AUG. The in vitro transcript of this plasmid when transfected into a cell with replicon RNA will produce the VEE glycoproteins. Co-electroporation of both of these helper RNAs into a cell with replicon RNA results in production of infectious particles containing only replicon RNA.

Other than the 5' and 3' ends and the 26S promoters (40 nucleotides) of these helper RNAs, the only sequence in common between the capsid and glycoprotein helpers is the sequence from 8389 to 8494 (105 nucleotides).

EXAMPLE 4

Results

The influenza HA gene, the GFP gene (cloned from Aquoria victoria jellyfish DNA by Chalfie and coworkers, Science 263:802 (1994)), the Lassa fever virus N protein gene and the Lassa fever virus envelope glycoprotein gene, have been inserted individually into the VEE replicon and expressed successfully in cultured BHK cells. Detection of protein expression was by specific fluorescent antibody binding, except in the case of GFP, which autofluoreses when exposed to light in the range of 340–490 nm. When GFP-replicon RNA alone is electroporated into BHK cells and expression is assayed by fluorescence, greater than 95% of the cells contain active GFP. Expression levels of Lassa fever N protein in BHK cells are measured following polyacrylamide gel electrophoresis of transfected cell lysates and image analysis with NIH Image Version 1.52 on a Coomassie stained gel. Levels range from 15% to 19% of total cell protein.

GFP is packaged into infectious defective particles by coelectroporation of GFP replicon RNA and V3014Δ520-7505(93%) helper RNA, and the titer is determined by infection of BHK cells and quantitative microscopy under 400 nm light, as well as FACS analysis. The yield of replicon particles is from 2 to $6 \times 10^7$ per mL under these conditions. Yields using various helper constructs to package the Lassa fever replicon RNA ranged from $1 \times 10^4$ infectious units/mL to $8 \times 10^7$ infectious units per mL.

The yield of infectious units from the tripartite electroporation with the two helper RNAs and Lassa fever N protein replicon RNA is greater than $3 \times 10^6$ per mL in the initial experiment, with no recombinants detected by two separate tests (limits of detection are 100 pfu/mL, and 20 fluorescent antibody VEE infectious units/mL). In addition, passage of the transfection supernatant onto fresh BHK cells gives no CPE after extended incubation.

Packaged replicons containing the Lassa fever N gene have been inoculated into mice and demonstrated to induce serum IgG antibody specific for N. The results are reported in FIG. 3. When a low dose inoculation is used, no serum IgG antibody specific for VEE is detected. However, there is VEE-specific IgG in the serum of a mouse inoculated with a higher dose, probably due to the replication-competent recombinants in the preparation (estimated by a plaque assay to be present at about $10^{-4}$-fold less than the titer of replicon particles). When both types of mice received a second identical dose of N replicon, both showed a significant boost in anti-N titer. See FIG. 3. The results suggest that the presence of anti-VEE antibody in the serum does not prevent boosting of the humoral response to the heterologous antigen. Also, the low dose boost still does not produce a consistently detectable titer against VEE. The results demonstrate that the packaged replicons can elicit a measurable immune response to the heterologous antigen, and can be used to boost the immune response in previously primed animals.

EXAMPLE 5

Additional Attenuated Virus Constructs

The constructs are prepared according to the methods set forth in Example 3 above, with the exception that the capsid gene of the helper is also subjected to site-directed mutagenesis. The altered capsid protein provides additional assurance that recombination to produce the virulent virus will not occur. The altered capsid protein gene that could function in the particle assembly but not in autoproteolysis would provide helper function for production of replicon particles, but would not produce a viable recombinant. The capsid residues required for proteolytic function are known. See Strauss, et al., *Seminars in Virology* 1:347 (1990).

In cases where vaccination with two immunogens provides improved protection against disease compared to vaccination with only a single immunogen, a double-promoter replicon would ensure that both immunogens are produced in the vaccinee. Such a replicon would be the same as the one described above, except that it would contain two copies of the 26S RNA promoter followed by two different multiple cloning sites, to allow for the insertion and expression of two different heterologous proteins. Another strategy would be to insert the IRES sequence from the picornavirus, EMC virus, between the two heterologous genes downstream from the single 26S promoter of the replicon described above, thus leading to translation of two immunogens from the single replicon transcript in the same cell.

The foregoing is illustrative of the present invention and is not to be construed as limiting thereof. The invention is defined by the following claims, with equivalents of the claims to be included therein.

That which is claimed is:

1. A helper cell for producing an infectious, defective alphavirus particle, comprising, in an alphavirus-permissive cell:

(a) an alphavirus replicon RNA, wherein the alphavirus is selected from the group consisting of Sindbis virus, Semliki Forest virus, Venezuelan Equine Encephalitis Virus, and South African Arbovirus No. 86; wherein the replicon RNA comprises the alphavirus packaging signal, a heterologous RNA sequence, and a sequence encoding at least one of the alphavirus structural proteins, wherein the replicon RNA furthermore lacks a sequence encoding at least one of the alphavirus structural proteins; and (b) at least one separate helper RNA encoding the structural protein(s) absent from the replicon RNA, said helper RNA(s) lacking the alphavirus packaging signal; wherein the combined expression of the replicon RNA and the helper RNA(s) produces an assembled alphavirus particle which comprises a heterologous RNA sequence, is able to infect a cell, and is unable to complete viral replication in the absence of helper RNA due to the absence of the structural protein coding sequence in the packaged replicon.

2. The helper cell according to claim 1, wherein said replicon RNA encodes the alphavirus capsid protein, and wherein said at least one separate helper RNA(s) encodes the alphavirus E1 glycoprotein and the alphavirus E2 glycoprotein.

3. The helper cell according to claim 1, wherein said alphavirus is Venezuelan Equine Encephalitis virus.

4. The helper cell according to claim 3, wherein at least one of said helper RNA and said replicon RNA includes at least one attenuating mutation selected from the group consisting of codons at E2 amino acid position 76 which specify an attenuating amino acid, codons at E2 amino acid position 120 which specify an attenuating amino acid, codons at E2 amino acid position 209 which specify an attenuating amino acid, codons at E1 amino acid 272 which specific an attenuating mutation, codons at E1 amino acid 81 which specify an attenuating mutation, codons at E1 amino acid 253 which specify an attenuating mutation, and the deletion of E3 amino acids 56–59.

5. The helper cell according to claim 1, wherein said alphavirus is South African Arbovirus No. 86.

6. The helper cell according to claim 5, wherein at least one of said helper RNA and said replicon RNA includes at least one attenuating mutation selected from the group consisting of codons at nsP1 amino acid position 538 which specify an attenuating amino acid, codons at E2 amino acid position 304 which specify an attenuating amino acid, codons at E2 amino acid position 314 which specify an attenuating amino acid, codons at E2 amino acid position 372 which specify an attenuating amino acid, codons at E2 amino acid position 376 which specify an attenuating amino acid, codons at nsP2 amino acid position 96 which specify an attenuating amino acid, and codons at nsP2 amino acid position 372 which specify an attenuating amino acid.

7. The helper cell according to claim 1, wherein said alphavirus is Semliki Forest virus.

8. The helper cell according to claim 1, wherein said helper RNA and said replicon RNA both include a promoter.

9. The helper cell according to claim 1, wherein said replicon RNA includes a promoter.

10. The helper cell according to claim 8 or 9, wherein said promoter is a Venezuelan Equine Encephalitis virus 26S subgenomic promoter.

11. The helper cell according to claim 1, wherein said inserted heterologous RNA is selected from the group consisting of RNA encoding proteins and RNA encoding peptides.

12. A method of making infectious, defective, alphavirus particles, comprising:

providing a helper cell according to claim 1;

producing said alphavirus particles in said helper cell; and then collecting said alphavirus particles from said cell.

13. The method according to claim 12, wherein said alphavirus replicon RNA and said at least one separate helper RNA are introduced into said helper cell by electroporation.

14. Infectious alphavirus particles produced by the method of claim 12.

15. A pharmaceutical formulation comprising infectious alphavirus particles according to claim 14 in an effective immunogenic amount in a pharmaceutically acceptable carrier.

16. A helper cell for producing an infectious, defective alphavirus particle, comprising an alphavirus-permissive cell transfected with RNAs comprising:

(a) an alphavirus replicon RNA, wherein the alphavirus is selected from the group consisting of Venezuelan Equine Encephalitis Virus and South African Arbovirus No. 86; wherein the replicon RNA comprises the alphavirus packaging signal, a heterologous RNA sequence, wherein the replicon RNA furthermore lacks sequences encoding alphavirus structural proteins; and (b) at least a first and second helper RNAs separate from said replicon RNA and separate from each other, said first and second helper RNAs encoding the structural proteins absent from the replicon RNA;

with said first helper RNA encoding at least one alphavirus structural protein and not encoding at least one other alphavirus structural protein;

with said second helper RNA not encoding said at least one alphavirus structural protein encoded by said first helper RNA and encoding said at least one other alphavirus structural protein not encoded by said first helper RNA;

and with said first and second helper RNAs lacking the alphavirus packaging signal;

wherein the combined expression of the replicon RNA and the helper RNAs produces an assembled alphavirus particle which comprises a heterologous RNA sequence, is able to infect a cell, and is unable to complete viral replication in the absence of the helper RNAs due to the absence of the structural protein coding sequence in the packaged replicon.

17. The helper cell according to claim 16, wherein said first helper RNA encodes both the alphavirus E1 glycoprotein and the alphavirus E2 glycoprotein, and wherein said second helper RNA encodes the alphavirus capsid protein.

18. The helper cell according to claim 16, wherein said alphavirus is Venezuelan Equine Encephalitis virus.

19. The helper cell according to claim 16, wherein said alphavirus is South African Arbovirus No. 86.

20. The helper cell according to claim 18, wherein at least one of said first helper RNA and said second helper RNA includes at least one attenuating mutation selected from the group consisting of codons at E2 amino acid position 76 which specify an attenuating amino acid, codons at E2 amino acid position 120 which specify an attenuating amino acid, codons at E2 amino acid position 209 which specify an attenuating amino acid, codons at E1 amino acid 272 which specify an attenuating mutation, codons at E1 amino acid 81 which specify an attenuating mutation, codons at E1 amino acid 253 which specify an attenuating mutation, and the deletion of E3 amino acids 56–59.

21. The helper cell according to claim 19, wherein at least one of said replicon RNA, said first helper RNA and said second helper RNA includes at least one attenuating mutation selected from the group consisting of codons at nsP1 amino acid position 538 which specify an attenuating amino acid, codons at E2 amino acid position 304 which specify an attenuating amino acid, codons at E2 amino acid position 314 which specify an attenuating amino acid, codons at E2 amino acid position 372 which specify an attenuating amino acid, codons at E2 amino acid position 376 which specify an attenuating amino acid, codons at nsP2 amino acid position 96 which specify an attenuating amino acid, and codons at nsP2 amino acid position 372 which specify an attenuating amino acid.

22. The helper cell according to claim 16, wherein said first helper RNA and said second helper RNA both include a promoter.

23. The helper cell according to claim 16, wherein said replicon RNA includes a promoter.

24. The helper cell according to claim 22 or 23, wherein said promoter is a Venezuelan Equine Encephalitis virus 26S subgenomic promoter.

25. The helper cell according to claim 16, wherein said inserted heterologous RNA is selected from the group consisting of RNA encoding proteins and RNA encoding peptides.

26. A method of making infectious, defective, alphavirus particles, comprising:

providing a helper cell according to claim 16;

producing said alphavirus particles in said helper cell; and then collecting said alphavirus particles from said cell.

27. The method according to claim 26, wherein said alphavirus replicon RNA and said at least first and second helper RNAs are introduced into said helper cell by electroporation.

* * * * *